United States Patent
Ross

(10) Patent No.: US 8,558,659 B2
(45) Date of Patent: Oct. 15, 2013

(54) URGENT ACCESS MEDICATION DISPENSING STATION

(75) Inventor: Graham Ross, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 932 days.

(21) Appl. No.: 12/511,897

(22) Filed: Jul. 29, 2009

(65) Prior Publication Data

US 2011/0030034 A1 Feb. 3, 2011

(51) Int. Cl.
*G08B 29/00* (2006.01)

(52) U.S. Cl.
USPC .......... 340/5.1; 340/5.2; 340/5.21; 340/5.31; 340/5.33; 340/5.7; 221/9; 221/12; 221/13; 221/15; 235/375; 235/380; 235/381; 235/382; 235/382.5; 700/232; 700/233; 700/237

(58) Field of Classification Search
USPC ........ 340/5.1–5.6, 1.1, 5.61–5.71, 10.1–10.6, 340/568.1, 5.8–5.85; 235/375–386; 700/237, 2, 9, 17, 215, 231, 244, 232, 700/233; 348/143, 156; 726/4, 5; 221/9–15
See application file for complete search history.

(56) References Cited

U.S. PATENT DOCUMENTS

| | | | | |
|---|---|---|---|---|
| 5,805,455 A * | 9/1998 | Lipps | | 700/231 |
| 6,116,461 A * | 9/2000 | Broadfield et al. | | 221/98 |
| 6,272,394 B1 * | 8/2001 | Lipps | | 700/231 |
| 6,385,505 B1 * | 5/2002 | Lipps | | 700/231 |
| 6,892,941 B2 * | 5/2005 | Rosenblum | | 235/383 |
| 2001/0032035 A1 * | 10/2001 | Holmes et al. | | 700/231 |
| 2003/0050732 A1 * | 3/2003 | Rivalto | | 700/237 |
| 2004/0108795 A1 * | 6/2004 | Meek et al. | | 312/218 |
| 2004/0113786 A1 * | 6/2004 | Maloney | | 340/568.1 |
| 2005/0062238 A1 * | 3/2005 | Broadfield et al. | | 280/1 |
| 2006/0071011 A1 * | 4/2006 | Varvarelis et al. | | 221/9 |
| 2006/0215024 A1 * | 9/2006 | Coonce et al. | | 348/143 |

FOREIGN PATENT DOCUMENTS

WO WO 2004/082359 9/2004
WO WO 2006/124211 11/2006

* cited by examiner

*Primary Examiner* — Steven Lim
*Assistant Examiner* — Sisay Yacob
(74) *Attorney, Agent, or Firm* — McDermott Will & Emery LLP

(57) ABSTRACT

A medical supply station is disclosed. The medical supply station includes a securable compartment configured to hold medical supplies, and a controller. The controller is responsive to access information and is configured to selectively permit access to the securable compartment when the access information indicates the securable compartment is authorized for access, and restrict access to the securable compartment when the access information indicates the securable compartment is not authorized for access. The medical supply station also includes a critical access module configured to, upon actuation, bypass the access information required by the controller and permit substantially immediate access to the securable compartment. The medical supply station further includes an image capturing device, coupled to the critical access module, configured to capture at least one image of an area proximal to the medical supply station in response to actuation of the critical access module.

21 Claims, 7 Drawing Sheets

URGENT ACCESS MEDICATION DISPENSING STATION

BACKGROUND

1. Field

The present disclosure generally relates to apparatus and methods for providing health care and, in particular, relates to providing care to a patient through controlled access to medical supplies, such as medications.

2. Description of the Related Art

It is well known in the medical community, and in particular, in hospitals, to provide centrally located medication and supply dispensing stations, such as wall cabinets, manually secured patient cassette drawers, and automated dispensing machines. Such generally accessible stations serve several functions including the distribution of medicines and supplies to patients. Access to medicines and supplies contained within the stations often require appropriate authorization to be provided by a user. Appropriate authorization often takes time, including manually entering identification information, such as a name and password. One disadvantage of requiring such authorization is that access to medicines and supplies within the station is delayed proportionately to the time required to enter the authorization information. In an urgent or emergency situation where medicine, or some other medical supply, contained within the station is required immediately, such delay in accessing the medicine may make a significant difference in the health of a patient. Alternatively, if no authorization were required to access medicines and supplies within the station, it would be difficult to identify a user and track use of the medicines and supplies.

SUMMARY

Embodiments of the medication station disclosed herein provide a critical access module that allows a user to gain substantially immediate access to medicine and supplies within the medication station without the need to enter authorization information. Access to the medicines and supplies is tracked by an image capturing device that is activated by the use of the critical access module.

According to certain embodiments of the present disclosure, a medical supply station is provided. The medical supply station includes at least one securable compartment configured to hold medical supplies, and a controller. The controller is responsive to access information and is configured to selectively permit access to the at least one securable compartment when the access information indicates the at least one securable compartment is authorized for access. The controller is also configured to restrict access to the at least one securable compartment when the access information indicates the at least one securable compartment is not authorized for access. The medical supply station also includes a critical access module configured to, upon actuation, bypass the access information required by the controller and permit substantially immediate access to the at least one securable compartment. The medical supply station further includes an image capturing device, coupled to the critical access module, configured to capture at least one image of an area proximal to the medical supply station in response to actuation of the critical access module.

According to certain aspects of the present disclosure, a method, for urgent medical supply dispensing, is provided. The method includes determining if a critical access module of a medical supply station is actuated, and if the critical access module is actuated, bypassing access information required by a controller, configured to restrict access to at least one securable compartment configured to hold medical supplies, in order to permit substantially immediate access to the at least one securable compartment. The method also includes capturing at least one image of an area proximal to the medical supply station in response to actuation of the critical access module.

According to other embodiments of the present disclosure, a computer-readable medium having computer-executable instructions for causing a processor to execute instructions to control a medical supply station by performing certain steps is provided. The steps include determining if a critical access module of a medical supply station is actuated, and if the critical access module is actuated, bypassing access information required by a controller, configured to restrict access to at least one securable compartment configured to hold medical supplies, in order to permit substantially immediate access to the at least one securable compartment. The steps also include capturing at least one image of an area proximal to the medical supply station in response to actuation of the critical access module.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Figure 1A:
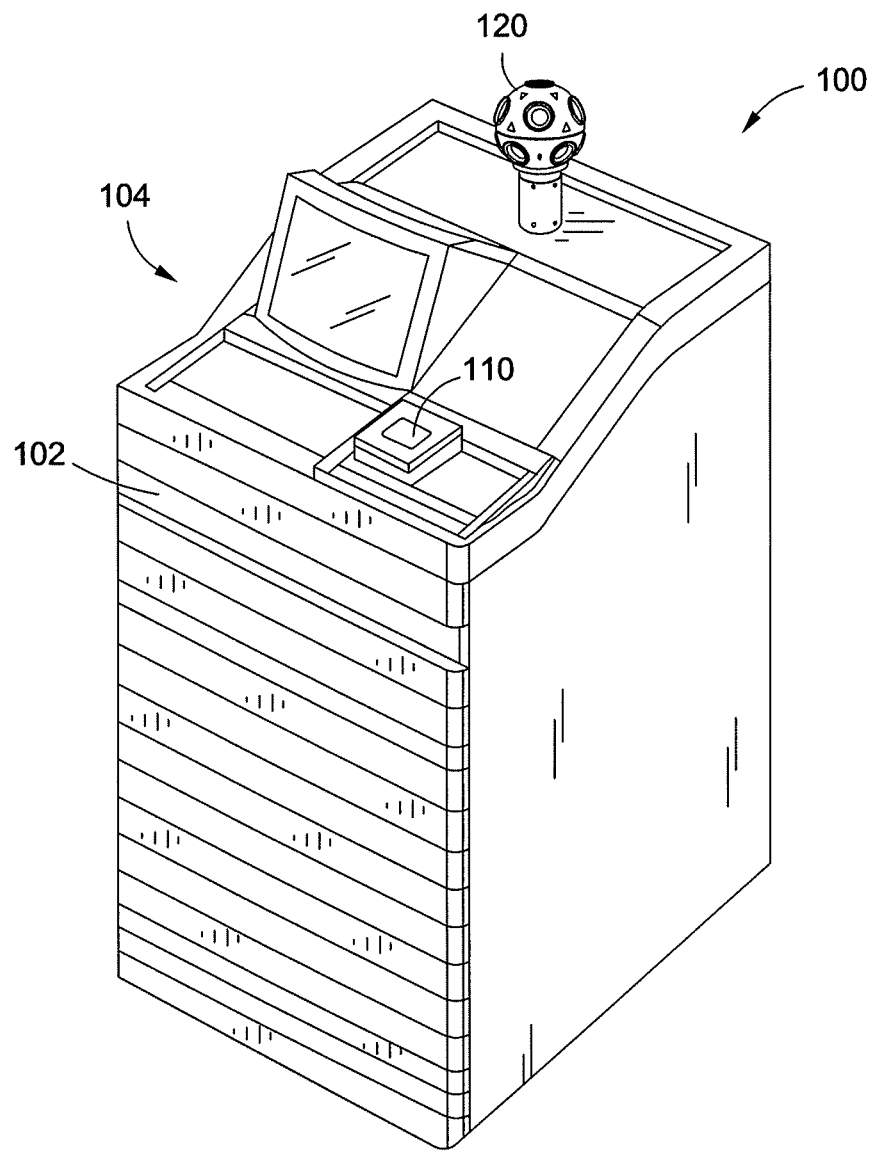
FIG. 1A illustrates a medication station according to certain embodiments.

FIG. 1A illustrates a medication station 100 according to certain embodiments. The medication station 100 includes at least one drawer (or securable compartment) 102, a controller 104, a critical access module 110, and an image capture device 120.

The medication station 100 is configured to provide for the dispensing of medications. The medication station 100, through its controller (e.g., electronic interface) 104, allows authorized users, such as caregivers, to access medications securely stored in the medication station 100, while restricting access to unauthorized users.

The medication station 100 includes a plurality of modular storage compartments, here shown as drawers 102. The number and type of drawers 102 used can be custom configured within the medication station 100 to match the medication and supply needs of the facility using the medication station 100. In certain embodiments, the configuration of the drawers 102 can be similar to the drawer configuration found in the presently commercially available product known as a MedStation automated medication management system from Cardinal Health, Inc., Dublin, Ohio. A MedStation system can be configured with different kinds of drawers 102 that include drawers with CUBIE receptacles, matrix drawers of different heights, and MiniDrawers.™ CUBIE, Matrix and Double Deep Matrix are terms understood by those skilled in the art. Medication stations that can be used, modified and/or configured according to the systems and methods disclosed herein are fully disclosed in U.S. Pat. Nos. 6,116,461 and 6,338,007, which are incorporated herein by reference. However, such stations are exemplary only, as the systems and methods disclosed herein may be employed with other dispensing stations.

The controller 104 is responsive to access information provided by a user. The controller 104 is configured to selectively permit access to the drawer 102 when the access information provided by the user indicates the user has access to the drawer 102, and the controller 104 restricts access to the drawer 102 when the user's access information indicates the user does not have access to the drawer 102. The controller 104 can be, for example, a computer terminal that includes a keyboard and a display. The basic functionality and configuration of the controller 104 can be found in U.S. Pat. Nos. 6,116,461 and 6,338,007 referred to above, as an example. In certain embodiments, the controller 104 comprises a transceiver configured to transmit, to a remote location, a signal indicating actuation of the critical access module 110.

Figure 1B:
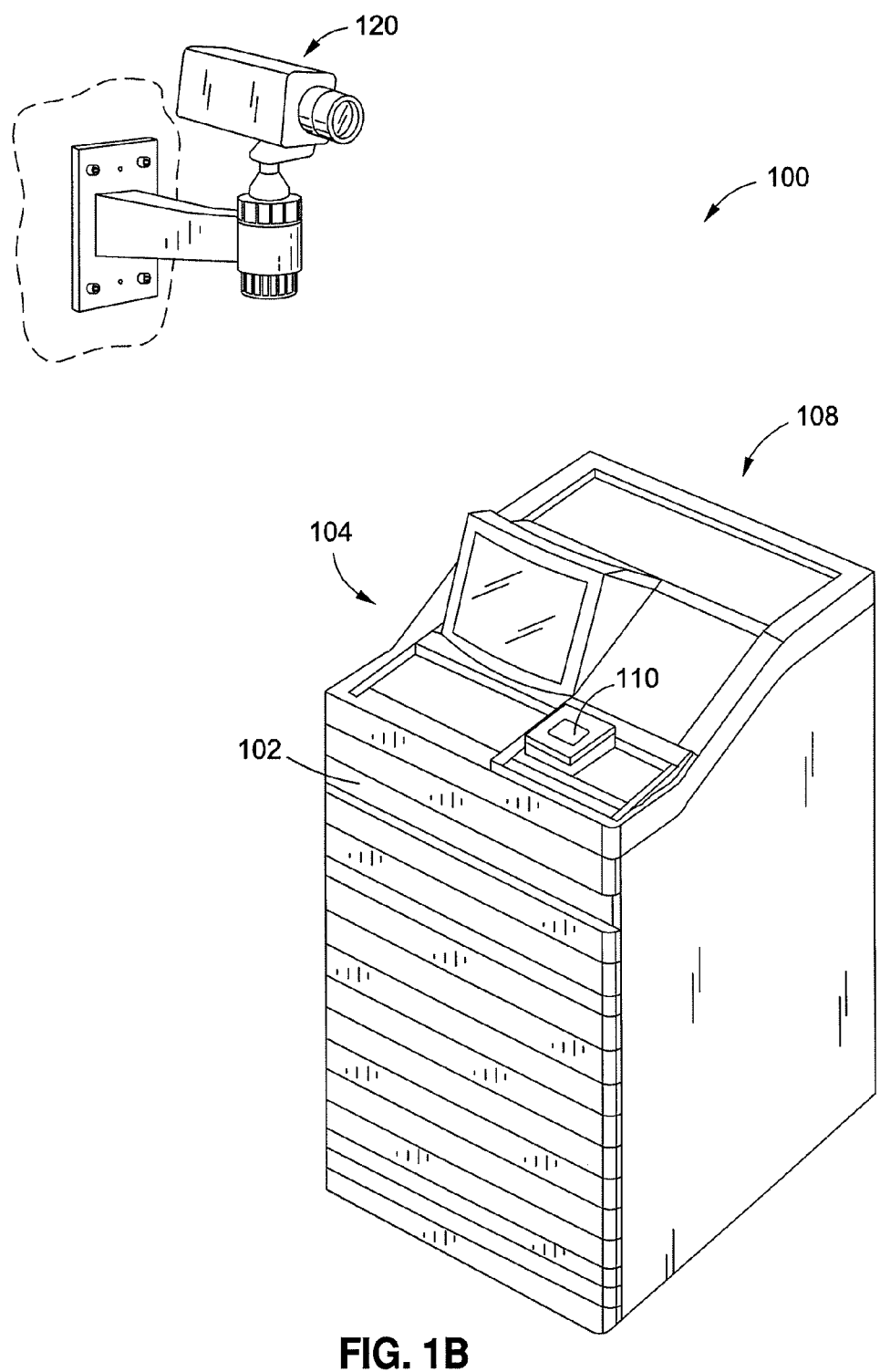
FIG. 1B illustrates another medication station according to certain embodiments.

The image capturing device 120 is coupled to the critical access module and configured to capture at least one image of an area proximal to the medication station 100. In certain embodiments, the image capturing device 120 begins to capture image and/or other data when the critical access module 110 is activated. The image capture device 120 is configured to capture still or moving images. In certain embodiments, the image capture device 120 is a still image camera configured to capture still images. In certain embodiments, the image capture device 120 is a video camera configured to capture moving images and audio (e.g., an audio/video stream). The image capture device 120 is configured to capture images in any number of directions and is positioned accordingly. For example, the image capture device 120 can be configured to capture images in the six principal directions: forward, backward, left, right, up, and down. In certain embodiments, the image capture device 120 can be configured to capture images in other directions depending on the target position of the image (e.g., down and to the right, to capture an image of the right side of an open drawer 102). In certain embodiments, the image capture device 120 may be placed apart from the chassis 108 of the medication station 100, such as on a wall or ceiling, as illustrated in FIG. 1B. In such embodiments, the image capture device 120 may be coupled to the chassis 108 of the medication station 100 by a wired or wireless connection. In certain embodiments, additional image capture devices 120 may be placed on and around the medication station 100 in order to obtain additional image data. In certain embodiments, the image capture device 120 has a field of view that includes at least one of an expected position of a user actuating the critical access module 110, an area surrounding the medical supply station 100, and the drawer 102.

In certain embodiments, the medication station 100 includes other devices to identify and/or track items that are removed from the medication station when the critical access module 110 is activated. For example, the medication station 100 can include radio-frequency identification (RFID) tags on the urgently needed items.

The critical access module 110 is configured to, upon actuation, bypass the access information required by the controller 104 to permit substantially immediate access to the drawer 102. The critical access module 110 can be activated in situations where a medication or supply contained by the medication station 100 needs to be accessed substantially immediately. For example, under normal circumstances (e.g., where urgent access is not required), the controller 104 would control access to the drawer 102, as discussed above. If, however, a need arises to urgently access the drawer 102, such as in an emergency, the critical access module 110 may bypass the controller 104 to provide access to the drawer 102.

In certain embodiments, activation of the critical access module 110 causes the medication station 100 to provide access to the drawer 102 through the controller 104 (e.g., by providing temporary authorization to the controller 104). In certain embodiments, the critical access module 110 provides access to a subset of drawers 102 included in the medication station 100, such as access to only one drawer 102. In certain embodiments, after a period of time transpires from the activation of the critical access module 110, the controller 104 causes the medication station 100 to restrict access to all drawers 102 as a safety precaution.

Figure 2A:
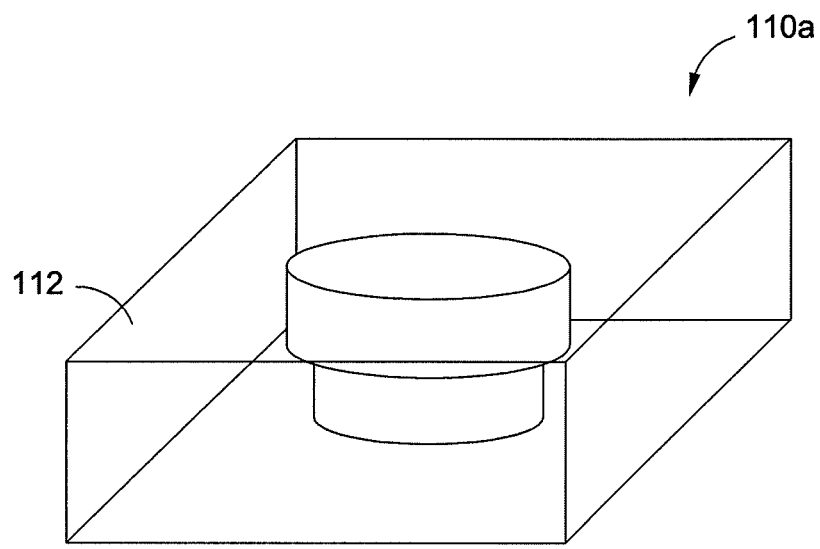
FIGS. 2A-2B illustrate critical access modules configured to be used with the medication station of FIG. 1A.

In certain embodiments, the critical access module 110 is a push button, as illustrated in FIG. 2A. The push button critical access module 110a is housed within a container 112 in order to inhibit accidental activation. The container 112 can, for example, be made of easily breakable plastic or glass. When pressed, the push button access module 110a is activated, thereby providing access to the drawer 102 in the medication station 100 that contains the urgently needed items.

Figure 2B:
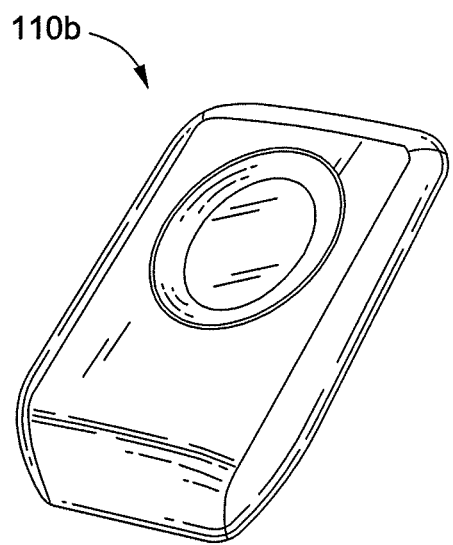

In certain embodiments, the critical access module 110 includes a biometric identification device, as illustrated in FIG. 2B. The biometric critical access module 110b can be, for example, a fingerprint reader. When the fingerprint of an authorized user is provided to the biometric critical access module 110b, the biometric critical access module 110b provides access to the drawer 102 in the medication station 100 that contains the urgently needed items. By providing a critical access module 110 that is configured to identify a user, the medication station 100 can prohibit the user from activating the critical access module 110 of other medication stations 100 for a certain period of time in order to prohibit unauthorized or unnecessary access of items (e.g., an authorized user attempting to unnecessarily obtain and collect urgent access items from multiple medication stations). In certain embodiments, the biometric critical access module 110b records the identity of a user attempting to actuate the biometric critical access module 110b. In certain embodiments, the biometric critical access module 110b provides access to the drawer 102 in the medication station 100 that contains the urgently needed items to an authorized user without recording the identity of the authorized user.

In certain embodiments not illustrated, the critical access module 110 can be another type of activator, such as a switch, trigger, or sensor. In certain embodiments not illustrated, the critical access module 110 can be another type of identification device. For example, the critical access module 110 can be an RFID reader, real time locating system (RTLS) module, key reader, infrared receiver, facial identifier, voice authenticator, or a magnetic stripe reader (e.g., activated by swiping a magnetic card).

In certain embodiments, the medication station may include a secondary access module (not illustrated) to provide an additional level of authorization to the critical access module 110. The secondary access module may be a device that facilitates rapid authentication, such as a RFID reader or magnetic stripe reader. By providing a second level of authorization in addition to the critical access module 110, an additional form of tracking and/or authorization may be provided.

Figure 3:
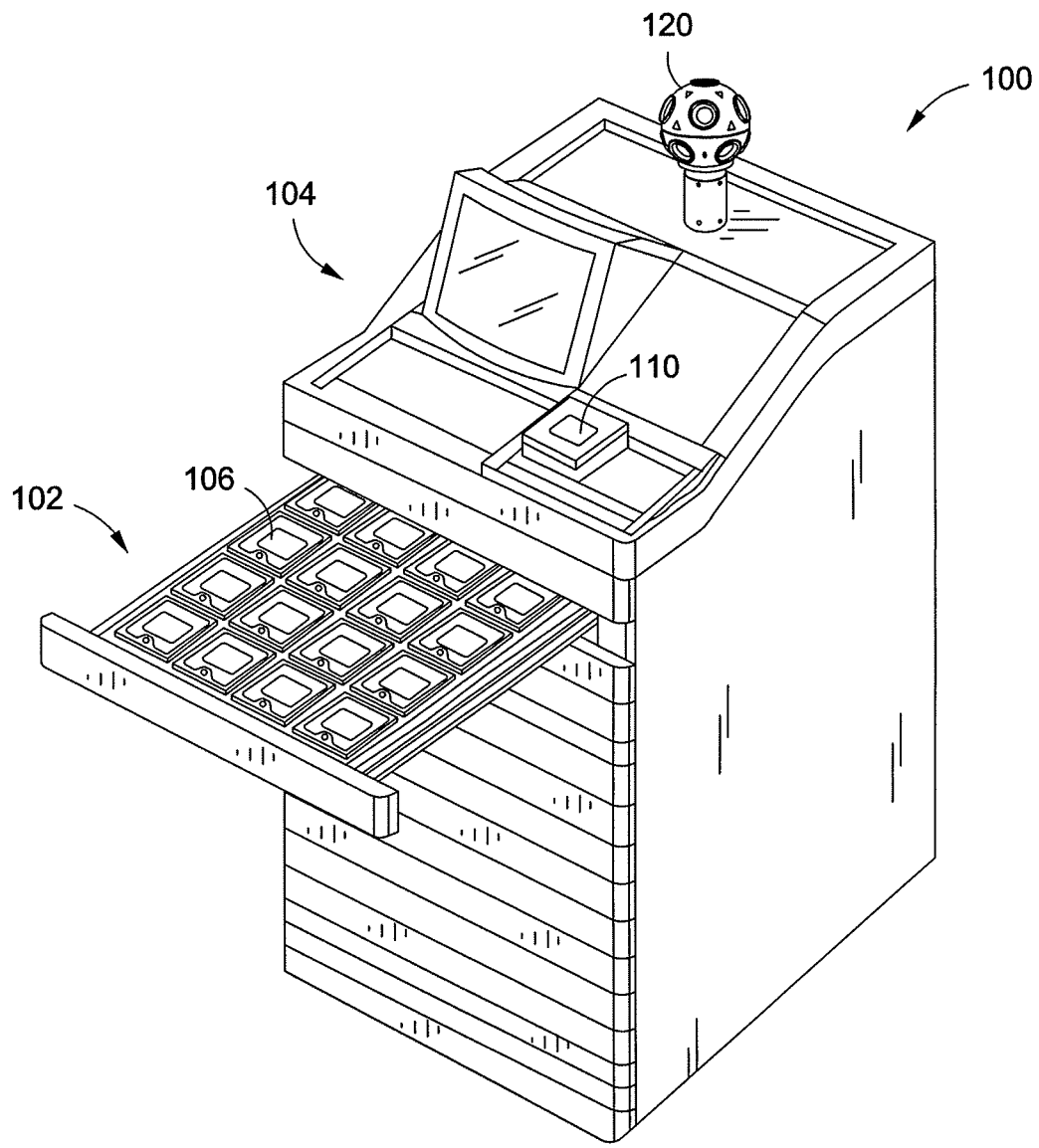
FIG. 3 illustrates the medication station of FIG. 1A after the critical access module has been activated.

FIG. 3 illustrates the medication station 100 of FIG. 1A after the critical access module 110 has been activated and access to the drawer 102 has been provided. The drawer 102 contains items, such as medicines or supplies, which are urgently needed by a user. Medical supplies can include medications. In certain embodiments, medical supplies are limited to medications. The items can be stored in any one of the containers 106 in the drawer 102. The container 106 containing the urgently needed items may, in certain embodiments, be indicated by a visual or audible indicator in order to direct the user to the container 106. In certain embodiments, the visual or audible indicator may be provided by a display or speaker of the controller 104. In certain embodiments, the container 106 containing the urgently needed items may be indicated by a lid of the container 106 popping up or the drawer 102 containing the container 104 popping out.

In the embodiment illustrated in FIG. 3, the image capture device 120 is configured to record images and/or audio related to the accessing of the container 106 because the critical access module 110 has been activated. By recording activity in and around the area of the medication station 100 during the access of the urgently needed items, the image capture device 120 provides a resource for identifying and tracking access to the items, as the standard authorization and tracking resources of the controller 104 have been bypassed.

Figure 4:
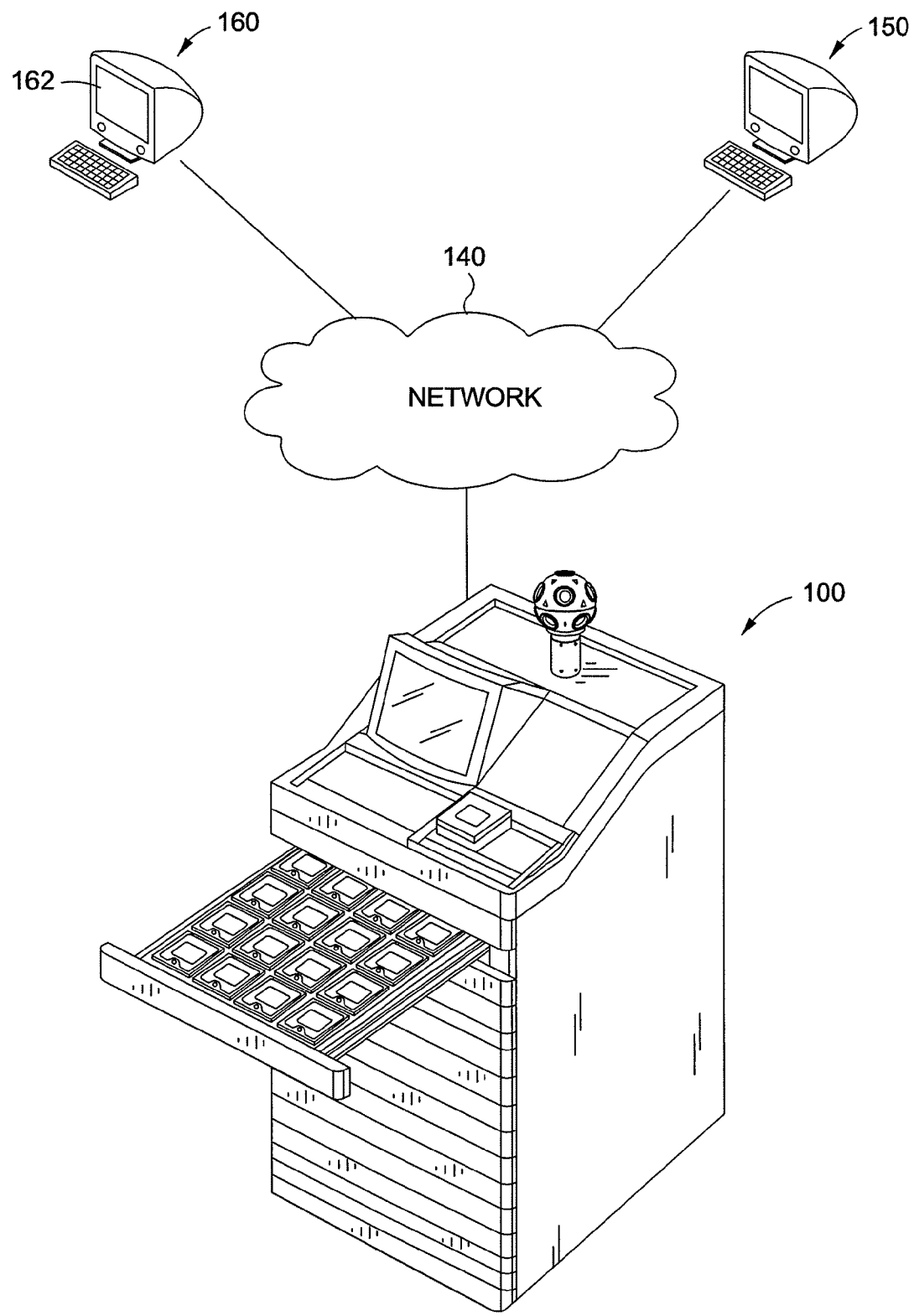
FIG. 4 illustrates the medication station of FIG. 1A coupled to a security network.

The images and other data recorded by the image capture device 120 can be transmitted over a network 140 to remote locations, such as a security terminal 150 and a pharmacy terminal 160, as illustrated in FIG. 4. In certain embodiments, other devices may be connected to the network 140. Each of the medication station 100, the security terminal 150, and pharmacy terminal 160 can be connected to the network 140 via a wired or wireless connection. The network 140 can be a local area network, wide area network, and may be, for example, the Internet. In certain embodiments, in addition to image data, an alert (e.g., "Crisis in Operating Room 3") may be transmitted by the medication station 100 to the security terminal 150 or the pharmacy terminal 160.

By providing image data to the security terminal 150, a user of the security terminal 150 can identify who has activated the critical access module 110 of the medication station and take appropriate action if the critical access module 110 has been activated inappropriately (e.g., by an unauthorized user). By providing image data to the pharmacy terminal 160, a pharmacist or pharmacy technician can track and determine the need to replenish the items which were urgently accessed.

Figure 5:
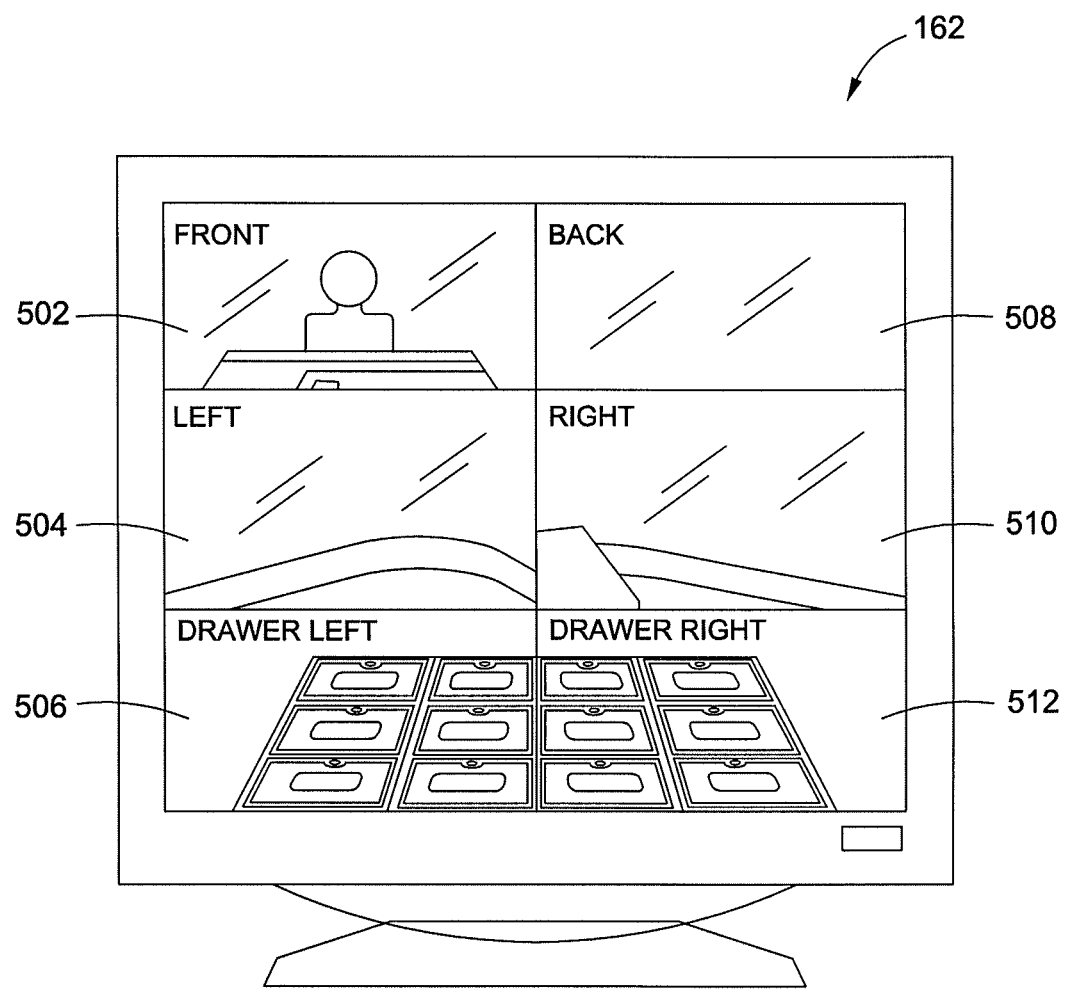
FIG. 5 illustrates images transmitted by the medication station of FIG. 1A to a remote viewing location.

Various types of image data can be provided to a remote terminal, such as the pharmacy terminal 160, as illustrated in FIG. 5. FIG. 5, which illustrates a display for the pharmacy terminal 160, includes an image 502 representing the front side of the medication station 100 (e.g., showing the user who activated the critical access module 110), an image 504 representing the left side of the medication station 100, an image 506 representing the left portion of the drawer 102 of the medication station 100, an image 508 representing the back side of the medication station 100, an image 510 representing the right side of the medication station 100, and an image 512 representing the right portion of the drawer 102 of the medication station 100.

Figure 6:
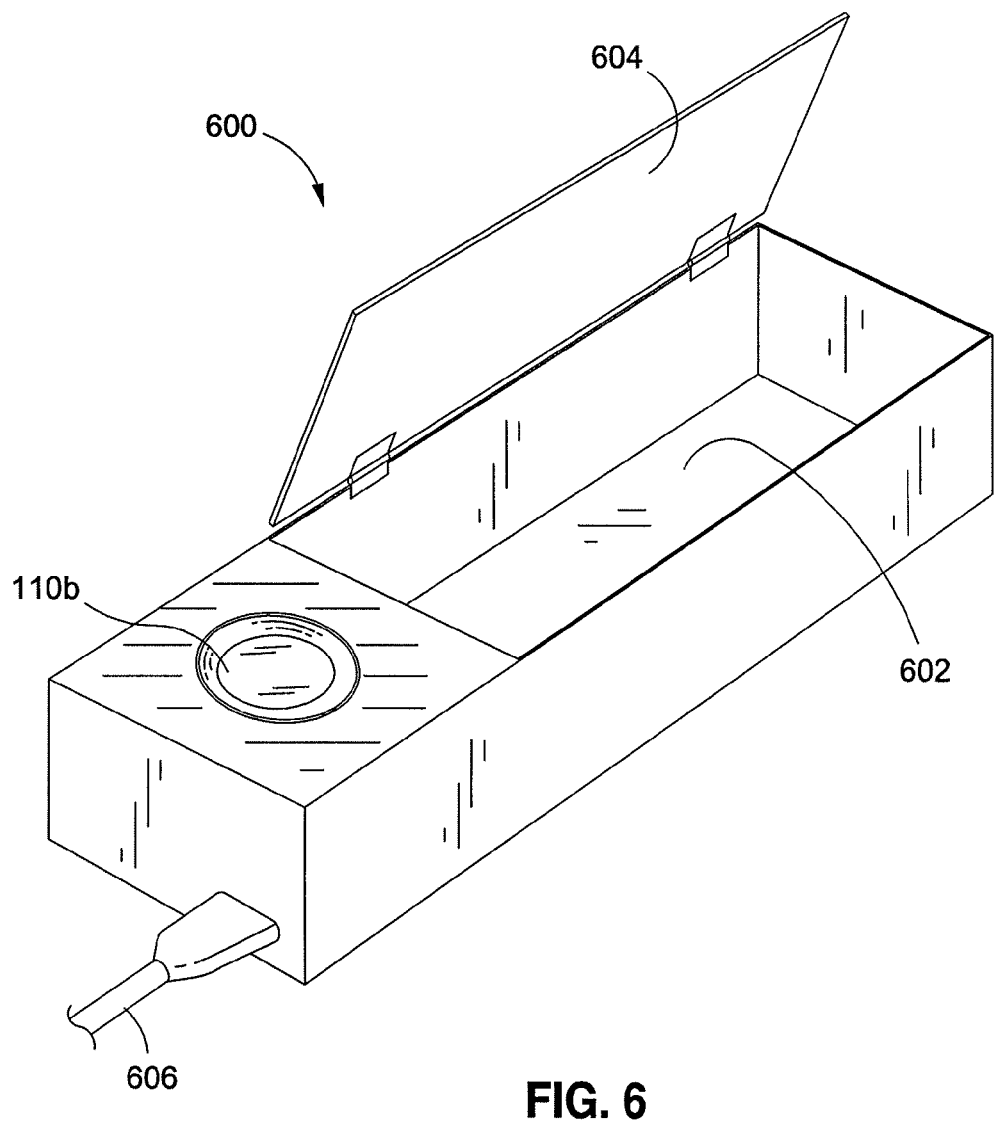
FIG. 6 illustrates a further medication station according to certain embodiments.

FIG. 6 illustrates a further medication station 600 according to certain embodiments. The medication station 600 includes a securable compartment 602 whose access is restricted by a lid 604, a critical access module 110b, and a connection 606 to a remote device. The medication station 600 is configured to provide for the urgent dispensing of medications. The medication station 600, through its critical access module 110b (illustrated here as a biometric fingerprint reader), allows authorized users, such as caregivers, urgent access to medications securely stored in the securable compartment 602, while restricting access to unauthorized users. The remote device connection 606 of the medication station 600 is configured to communicate with the controller of a larger dispensing station, such as, for example, the exemplary medication stations described above with reference to U.S. Pat. Nos. 6,116,461 and 6,338,007. However, such stations are exemplary only, as the medication station 600 disclosed herein may be employed with other dispensing stations.

By allowing the medication station 600 to communicate with other dispensing stations, the medication station 600, can, for example, be placed on or near an existing dispensing station to add a resource for urgent access to medications or other items near the dispensing station. The remote device connection 606 may further provide other information to the dispensing station or remote device, such as, for example, the date, time, user identification, and item type urgently dispensed from the medication station 600. In certain embodiments, the medication station 600 can include an image capture device 120 as disclosed above.

The embodiments of the present disclosure allow access to a medication station on an urgent basis. This can be achieved while providing a measure of security and authorization control. The emergency access permits caregivers to provide urgently needed supplies more quickly in emergency situations, thereby increasing safety for patients.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A medical supply station comprising:
   a plurality of securable compartments configured to hold medical supplies;
   a controller, responsive to access information, configured to:
      selectively permit access to one of the plurality of securable compartments when the access information indicates the one securable compartment is authorized for access; and
      restrict access to the one securable compartment when the access information indicates the one securable compartment is not authorized for access;
   a critical access module configured to, in response to actuation, bypass the access information required by the controller and permit substantially immediate access limited to the one securable compartment from among the plurality of securable compartments; and an image capturing device, coupled to the critical access module, and configured to capture at least one image of an area proximal to the medical supply station in response to actuation of the critical access module, wherein the controller is configured to restrict access to the one securable compartment by the critical access module after a predetermined number of actuations of the critical access module.

2. The station of claim 1, wherein the one securable compartment comprises an indicator coupled to the critical access module, and wherein the indicator is activated upon actuation of the critical access module to indicate the one securable compartment.

3. The station of claim 1, wherein the image capturing device comprises a camera.

4. The station of claim 1, wherein the image capturing device comprises a video camera.

5. The station of claim 1, wherein the image capturing device outputs the at least one image to a remote location.

6. The station of claim 1, wherein the image capturing device includes a field of view that includes at least one of an expected position of a user actuating the critical access module, an area surrounding the medical supply station, and the one securable compartment.

7. The station of claim 1, wherein the critical access module comprises a switch.

8. The station of claim 1, wherein the critical access module comprises a biometric device.

9. The station of claim 8, wherein the critical access module stores an identity of a user attempting to actuate the critical access module.

10. The station of claim 1, wherein the critical access module is responsive to second access information configured to be input into to the critical access module substantially immediately.

11. The station of claim 10, wherein the second access information comprises biometric input.

12. The station of claim 10, wherein the second access information comprises magnetic input.

13. The station of claim 10, wherein the second access information comprises information received from a real time locating system.

14. The station of claim 1, further comprising a transceiver configured to transmit, to a remote location, a signal indicating actuation of the critical access module.

15. A medical supply station comprising:
a plurality of securable compartments configured to hold medical supplies;
a critical access module configured to, in response to actuation by a user, permit substantially immediate access limited to one of the plurality of securable compartments;
a transceiver configured to provide identification information of the user to an item dispensing device; and
a controller configured to restrict access to the one of the plurality of securable compartments by the critical access module after a predetermined number of actuations of the critical access module.

16. The station of claim 15, further comprising an image capturing device, coupled to the critical access module, and configured to capture at least one image of an area proximal to the medical supply station in response to actuation of the critical access module.

17. A method, for urgent medical supply dispensing, comprising:
determining if a critical access module of a medical supply station is actuated;
in response to when the critical access module is actuated, bypassing access information required by a controller, configured to restrict access to one of a plurality of securable compartments configured to hold medical supplies, in order to permit substantially immediate access limited to the one securable compartment from among the plurality of securable compartments;
capturing at least one image of an area proximal to the medical supply station in response to actuation of the critical access module; and
restricting access to the one securable after a predetermined number of actuations of the critical access module.

18. The method of claim 15, further comprising activating an indicator configured to indicate the one securable compartment upon actuation of the critical access module.

19. The method of claim 15, further comprising outputting the at least one image to a remote location.

20. The method of claim 15, wherein access information required by the controller is bypassed if both the critical access module is actuated and second access information is provided to the critical access module.

21. A non-transitory computer-readable medium having computer-executable instructions for causing a processor to execute instructions to control a medical supply station by performing steps comprising:
determining if a critical access module of a medical supply station is actuated;
in response to when the critical access module is actuated, bypassing access information required by a controller, configured to restrict access to a plurality of securable compartments configured to hold medical supplies, in order to permit substantially immediate access limited to one securable compartment from among the plurality of securable compartments;
capturing at least one image of an area proximal to the medical supply station in response to actuation of the critical access module; and
restricting access to the one securable after a predetermined number of actuations of the critical access module.

* * * * *